US012226116B2

(12) United States Patent
Gras et al.

(10) Patent No.: US 12,226,116 B2
(45) Date of Patent: Feb. 18, 2025

(54) ULTRASONIC TIP WITH PROTRUSION DEFINING A PREASPIRATION HOLE

(71) Applicant: Stryker European Operations Holdings LLC, Kalamazoo, MI (US)

(72) Inventors: Guillaume Gras, Bienne (CH); Cathal Heavey, Midleton (IE); Conor McCarthy, West Cork (IE)

(73) Assignee: Stryker European Operations Holdings LLC, Portage, MI (US)

( * ) Notice: Subject to any disclaimer, the term of this patent is extended or adjusted under 35 U.S.C. 154(b) by 847 days.

(21) Appl. No.: 17/278,682

(22) PCT Filed: Sep. 23, 2019

(86) PCT No.: PCT/US2019/052451
§ 371 (c)(1),
(2) Date: Mar. 23, 2021

(87) PCT Pub. No.: WO2020/068678
PCT Pub. Date: Apr. 2, 2020

(65) Prior Publication Data
US 2021/0393286 A1  Dec. 23, 2021

Related U.S. Application Data

(60) Provisional application No. 62/735,440, filed on Sep. 24, 2018.

(51) Int. Cl.
*A61B 17/32* (2006.01)
(52) U.S. Cl.
CPC ............... *A61B 17/320068* (2013.01); *A61B 2017/32007* (2017.08); *A61B 2017/320072* (2013.01);
(Continued)

(58) Field of Classification Search
CPC .. A61B 17/320068; A61B 2017/32007; A61B 2017/320072; A61B 2017/320084;
(Continued)

(56) References Cited

U.S. PATENT DOCUMENTS

| 3,589,363 A | 6/1971 | Banko et al. |
| 4,493,694 A | 1/1985 | Wuchinich |

(Continued)

FOREIGN PATENT DOCUMENTS

| CN | 101390785 A | 3/2009 |
| CN | 101772325 A | 7/2010 |

(Continued)

OTHER PUBLICATIONS

English language abstract and machine-assisted English translation for CN 101897615 A extracted from espacenet.com database on Dec. 30, 2023, 5 pages.

(Continued)

*Primary Examiner* — Kelly J Bekker
*Assistant Examiner* — Nasheha Baset
(74) *Attorney, Agent, or Firm* — Howard & Howard Attorneys PLLC

(57) ABSTRACT

An ultrasonic tip for use with a surgical handpiece to produce both longitudinal and torsional motion. The ultrasonic tip comprises a shaft having a longitudinal axis extending between proximal and distal ends having respective first and second diameters with the first diameter greater than the second diameter. The ultrasonic tip also comprises a cutting feature coupled to the distal end of the shaft. The shaft defines an aspiration lumen that extends along the longitudinal axis of the shaft. A protrusion on the shaft is positioned between the distal end and the proximal end of the shaft. A portion of the protrusion having a third diameter, and the third diameter is less than the first diameter and the (Continued)

third diameter is greater than the second diameter. An aperture is defined by the protrusion and in fluid communication with the aspiration lumen, and the protrusion reinforces an area surrounding the aperture.

27 Claims, 12 Drawing Sheets

(52) U.S. Cl.
CPC ............ *A61B 2017/320084* (2013.01); *A61B 2017/320098* (2017.08)

(58) Field of Classification Search
CPC ......... A61B 2017/320098; A61B 2017/22018; A61B 2017/320074; A61B 2017/32008; A61B 2017/320089; A61B 2018/00035; A61B 2217/005; A61B 2217/007; A61B 17/16

See application file for complete search history.

(56) References Cited

U.S. PATENT DOCUMENTS

| | | | |
|---|---|---|---|
| 4,516,398 A | | 5/1985 | Wuchinich |
| 5,076,276 A | | 12/1991 | Sakurai et al. |
| 5,163,433 A | * | 11/1992 | Kagawa ........... A61B 17/22012 604/27 |
| 5,334,183 A | | 8/1994 | Wuchinich |
| 5,484,398 A | | 1/1996 | Stoddard |
| 5,562,609 A | | 10/1996 | Brumbach |
| 6,214,017 B1 | | 4/2001 | Stoddard et al. |
| 6,256,859 B1 | | 7/2001 | Stoddard et al. |
| 6,497,715 B2 | | 12/2002 | Satou |
| 6,511,454 B1 | | 1/2003 | Nakao et al. |
| 6,654,999 B2 | | 12/2003 | Stoddard et al. |
| 6,955,680 B2 | | 10/2005 | Satou et al. |
| 6,984,220 B2 | | 1/2006 | Wuchinich |
| 7,374,552 B2 | | 5/2008 | Wuchinich |
| 7,931,611 B2 | | 4/2011 | Novak et al. |
| 8,092,475 B2 | | 1/2012 | Cotter et al. |
| 8,303,530 B2 | | 11/2012 | Injev et al. |
| 8,512,340 B2 | | 8/2013 | Easley et al. |
| 9,044,261 B2 | | 6/2015 | Houser |
| 9,358,017 B2 | | 6/2016 | Rad |
| 2002/0026187 A1 | | 2/2002 | Swanson |
| 2004/0039311 A1 | | 2/2004 | Nita et al. |
| 2005/0124986 A1 | | 6/2005 | Brounstein et al. |
| 2006/0004396 A1 | * | 1/2006 | Easley ............... A61B 17/1659 606/169 |
| 2006/0235306 A1 | | 10/2006 | Cotter et al. |
| 2011/0105958 A1 | | 5/2011 | Babaev |
| 2013/0197363 A1 | | 8/2013 | Rankin et al. |
| 2016/0128707 A1 | | 5/2016 | Mikus et al. |
| 2018/0103976 A1 | | 4/2018 | Heavey |
| 2018/0200109 A1 | | 7/2018 | Chon et al. |
| 2018/0250031 A1 | | 9/2018 | Mikus et al. |

FOREIGN PATENT DOCUMENTS

| | | |
|---|---|---|
| CN | 101897615 A | 12/2010 |
| EP | 0768840 B1 | 12/2001 |
| EP | 2881058 A1 | 6/2015 |
| WO | 9524865 A1 | 9/1995 |
| WO | 00022995 A2 | 4/2000 |
| WO | 2015164753 A1 | 10/2015 |
| WO | 2018053223 A1 | 3/2018 |

OTHER PUBLICATIONS

International Search Report for Application No. PCT/US2019/052451 dated Jan. 8, 2020, 4 pages.

English language abstract for CN 101772325 A extracted from espacenet.com database on Jul. 16, 2024, 2023, 2 pages.

English language abstract for CN 101390785 A extracted from espacenet.com database on Nov. 7, 2024, 2 pages.

\* cited by examiner

ULTRASONIC TIP WITH PROTRUSION DEFINING A PREASPIRATION HOLE

RELATED APPLICATIONS

This patent application claims priority to and all the benefits of International Application No. PCT/US2019/052451 filed on Sep. 23, 2019 which claims priority to and all the benefits of U.S. Provisional Patent Application No. 62/735,440 filed on Sep. 24, 2018, which is herein incorporated by reference in its entirety.

BACKGROUND

As medical professionals strive to reduce the size of the incisions and the amount of recovery time required following surgical procedures, the sizes of medical instruments used in such procedures have become smaller. Medical instruments utilized in performing such surgical procedures may include the use of a cutting accessory, such as an ultrasonic tip. In performing a cutting, shaving, or shaping operation, the cutting accessory will be exposed to varying amounts of force, creating stresses within the cutting accessory. The cutting accessories may also be used in coordination with irrigation or aspiration, that is, suction, to reduce heat and/or remove debris at the surgical site. Irrigation may also be utilized as a cutting medium.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
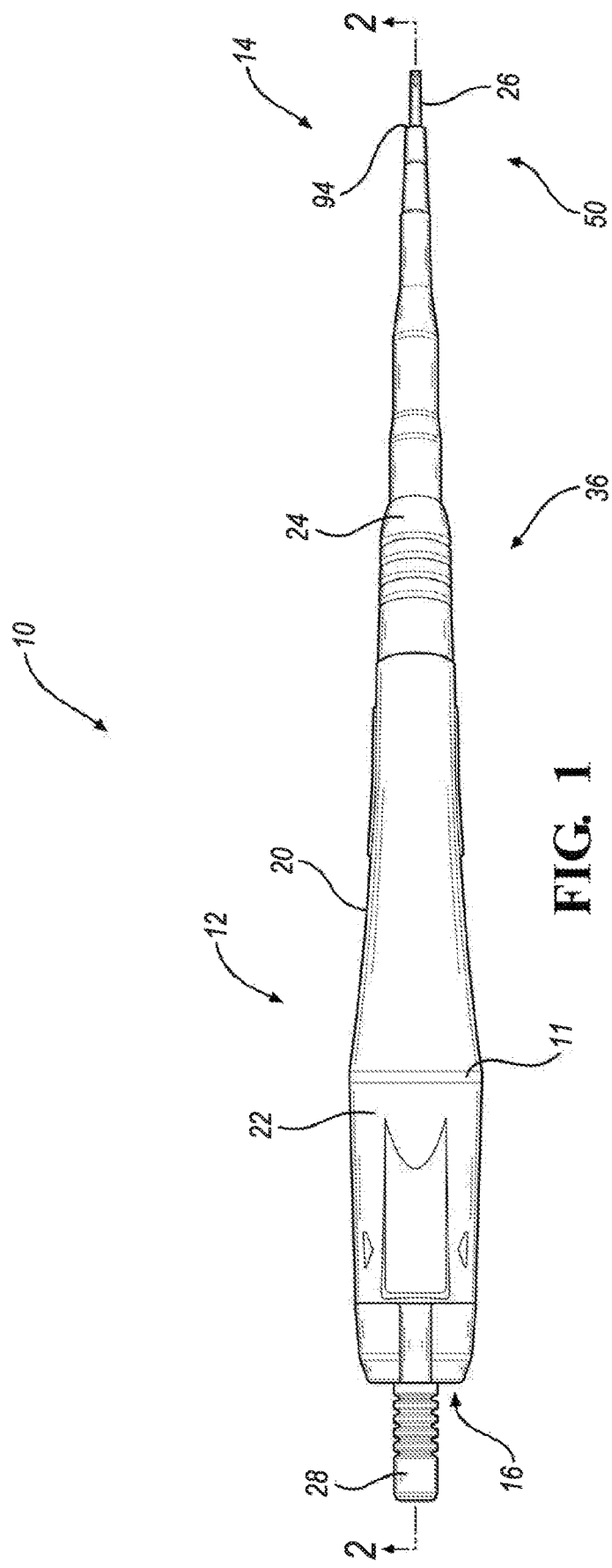
FIG. 1 is a top view of an ultrasonic surgical handpiece assembly.

One example of a surgical instrument that may utilize irrigation and/or aspiration systems is an ultrasonic surgical handpiece. Generally, one or more lines may be coupled to the ultrasonic surgical handpiece to supply irrigation and/or suction. The ultrasonic surgical handpiece may further comprise a sleeve comprising one or more lumens that may be utilized to direct fluid from an irrigation source toward the surgical site and/or the cutting accessory, i.e., the ultrasonic tip.

An ultrasonic tip is for use with a surgical handpiece to produce both longitudinal and torsional motion, the handpiece including an ultrasonic transducer disposed within a housing. The ultrasonic tip comprises a shaft, a cutting feature, and a protrusion. The shaft has a longitudinal axis extending between a proximal end and a distal end of the shaft. The proximal end has a first diameter. The distal end has a second diameter. The first diameter is greater than the second diameter. The shaft comprises a vibration conversion mechanism for converting a vibration energy transmitted from the ultrasonic transducer into a composite vibration composed of a longitudinal vibration along the longitudinal axis and a torsional vibration. The cutting feature is coupled to the distal end of the shaft. An aspiration lumen is defined by the shaft. The aspiration lumen is configured to extend along the longitudinal axis of the shaft. The aspiration lumen is configured to be placed in fluid communication with the handpiece. The protrusion is on the shaft and is positioned between the distal end and the proximal end. The protrusion is positioned distal to the vibration conversion mechanism along the longitudinal axis. A portion of the protrusion has a third diameter. The third diameter is less than the first diameter and the third diameter is greater than the second diameter. An aperture is defined by the protrusion. The aperture is in fluid communication with the aspiration lumen. The protrusion reinforces an area surrounding the aperture.

The proximal end of the shaft may comprise a coupling feature configured to removeably couple the shaft to the transducer of the handpiece.

The coupling feature may comprise a plurality of threads configured to couple to the transducer of the handpiece.

The vibration conversion mechanism may comprise one or more helical groove portions formed on an external surface of the shaft.

An axis of the aperture may be transverse to the longitudinal axis of the ultrasonic tip.

The cutting feature may comprise a cutting face facing in a direction at an angle equal to or less than 90 degrees to the longitudinal axis.

The cutting feature may have a cutting face arranged radially outward from the longitudinal axis. The cutting face may comprise one or more teeth.

The protrusion may comprise a first taper region, a median region, and a second taper region. An external surface of the median region may be generally parallel to the longitudinal axis. The median region may be disposed between the first taper region and the second taper region. The first taper region may be proximal to the median region and have a positive slope. The second taper region may be distal to the median region and have a negative slope.

The aspiration lumen may be open at the distal end and at the proximal end of the shaft.

An ultrasonic sleeve assembly is for use with a surgical handpiece comprising an ultrasonic transducer. The ultrasonic sleeve assembly comprises a cutting tip and an irrigation sleeve. The cutting tip comprises a shaft, a vibration conversion mechanism, a cutting feature and a protrusion. The shaft extends between a proximal end and a distal end. The proximal end comprises a coupling feature configured to removeably couple the shaft to the handpiece. The proximal end comprises a first diameter and the distal end comprises a second diameter. The first diameter is greater than the second diameter. The vibration conversion mechanism is for converting a vibration energy transmitted from the ultrasonic transducer into a composite vibration composed of a longitudinal vibration along a longitudinal axis and a torsional vibration. The cutting feature is coupled to the distal end of the shaft. An aspiration lumen is defined by the shaft and is configured to extend along the longitudinal axis of the shaft. The aspiration lumen is configured to be in fluid communication with the surgical handpiece when the shaft is coupled to the surgical handpiece. The protrusion is on the shaft and is positioned distal of the vibration conversion mechanism. A portion of the protrusion has a third diameter. The third diameter is less than the first diameter. The third diameter is greater than the second diameter. The protrusion is configured to strengthen the shaft. An aperture is defined by the protrusion and is in fluid communication with the aspiration lumen. The irrigation sleeve is configured to surround a portion of the shaft when the irrigation sleeve and the cutting tip are coupled to the handpiece. The irrigation sleeve defines a lumen comprising a proximal end and a distal end. The proximal end of the lumen comprises a coupling mechanism configured to removeably couple to the handpiece. The irrigation sleeve further defines an irrigation channel separate from the lumen. The irrigation channel has a distal end and a proximal end. The proximal end of the irrigation channel is configured to releasably couple to an irrigation source. The irrigation channel is configured to carry fluid to the lumen through an irrigation port. The irrigation port is in fluid communication with the irrigation channel and the lumen.

The coupling feature may comprise a plurality of threads configured to couple to the transducer of the handpiece.

The vibration conversion mechanism may comprise one or more helical groove portions formed on an external surface of the shaft.

The cutting feature may comprise a cutting face facing in a direction perpendicular to the longitudinal axis.

The aperture may be positioned in a radially opposed direction from the cutting face.

The cutting feature may have a cutting face arranged radially outward from the longitudinal axis. The cutting face may comprise one or more teeth.

The protrusion may comprise a first taper region, a median region, and a second taper region. An external surface of the median region may be generally parallel to the longitudinal axis. The median region may be disposed between the first taper region and the second taper region. The first taper region may be proximal to the median region and may have a positive slope. The second taper region may be distal to the median region and may have a negative slope.

The aspiration lumen may be open at the distal end and the proximal end of the shaft.

An ultrasonic cutting system for producing both longitudinal and torsional motion comprises a handpiece, a cutting tip and an irrigation sleeve. The handpiece comprises a transducer disposed within a housing. The cutting tip is coupled to the handpiece and comprises a shaft and a cutting feature. The shaft comprises a distal end and a proximal end. The proximal end comprises a coupling feature configured to removeably couple the shaft to the handpiece. The cutting feature is coupled to the distal end of the shaft. An aspiration lumen is defined by the shaft. The aspiration lumen is configured to extend along a longitudinal axis of the shaft. The aspiration lumen is in fluid communication with the handpiece. An aperture is in fluid communication with the aspiration lumen, and is located between the proximal end and the distal end of the shaft. The aperture has a proximal end and a distal end. An irrigation sleeve is coupled to the handpiece. The irrigation sleeve surrounds a portion of the shaft, and has a proximal end and a distal end. The irrigation sleeve defines a lumen. The proximal end of the irrigation sleeve has a coupling mechanism configured to removeably couple the irrigation sleeve to the handpiece. The irrigation sleeve further defines an irrigation channel comprising a distal end and a proximal end. The proximal end of the irrigation channel is configured to receive irrigation fluid from an irrigation source. An irrigation port is in fluid communication with the distal end of the irrigation channel. The irrigation port is configured to dispense irrigation fluid toward the shaft. The distal end of the irrigation sleeve is positioned proximal to the distal end of the shaft. The irrigation port is positioned proximal relative to the aperture along the longitudinal axis. The distal end of the irrigation sleeve is distal to the distal end of the aperture such that the irrigation sleeve encompasses an entirety of the aperture.

The distal end of the irrigation sleeve may extend beyond the distal end of the aperture in a distal direction along the longitudinal axis.

The coupling feature may comprise a plurality of threads configured to couple to the transducer of the handpiece.

The shaft may comprise a vibration conversion mechanism for converting a vibration energy transmitted from the transducer into a composite vibration composed of a longitudinal vibration along the longitudinal axis and a torsional vibration.

The vibration conversion mechanism may comprise one or more helical groove portions formed on an external surface of the shaft.

The cutting feature may comprise a cutting face facing in a direction perpendicular to the longitudinal axis.

The aperture may be positioned in a radially opposed direction from the cutting face.

The cutting feature may have a cutting face arranged radially outward from the longitudinal axis and wherein the cutting face comprises one or more teeth.

The aspiration lumen may be open at the distal end and the proximal end of the shaft.

An ultrasonic tip is for use with a surgical handpiece to produce both longitudinal and torsional motion, the surgical handpiece including an ultrasonic transducer. The ultrasonic tip comprises a shaft, a cutting feature and a protrusion. The shaft extends between a proximal end and a distal end. The proximal end has a first cross-sectional area and a second cross-sectional area. The first cross-sectional area is greater than the second cross-sectional area. The shaft comprises a vibration conversion mechanism for converting a vibration energy transmitted from the ultrasonic transducer into a composite vibration composed of a longitudinal vibration along a longitudinal axis and a torsional vibration. The cutting feature is coupled to the distal end of the shaft. An aspiration lumen is defined by the shaft. The aspiration lumen is configured to extend along the longitudinal axis of the shaft. The aspiration lumen is configured to be placed in fluid communication with the handpiece. The protrusion is on the shaft and is positioned between the distal end and the proximal end. The protrusion is positioned distal to the vibration conversion mechanism along the longitudinal axis. A portion of the protrusion has a third cross-sectional area. The third cross-sectional area is less than the first cross-sectional area. The third cross-sectional area is greater than the second cross-sectional area. An aperture is defined by the protrusion and is in fluid communication with the aspiration lumen. The protrusion reinforces an area surrounding the aperture.

An ultrasonic tip is for use with a surgical handpiece that includes an ultrasonic transducer disposed within a housing. The ultrasonic tip comprises a shaft, a cutting feature and a protrusion. The shaft comprises a distal region, an intermediate region and a proximal region. The intermediate region has a first diameter. The distal region has a second diameter. The first diameter is greater than the second diameter. The shaft comprises a vibration conversion mechanism for converting a vibration energy transmitted from the ultrasonic transducer into a composite vibration composed of a longitudinal vibration along a longitudinal axis and a torsional vibration. The cutting feature is coupled to the distal region of the shaft. A first lumen is defined by the shaft. The first lumen is configured to extend along the longitudinal axis of the shaft. The first lumen is configured to be placed in fluid communication with the handpiece. The protrusion is on the shaft and is positioned between the intermediate region and the distal region. The intermediate region is positioned between the protrusion and the vibration conversion mechanism. A portion of the protrusion has a third diameter. The third diameter is less than the first diameter, and the third diameter is greater than the second diameter. An aperture is defined by the protrusion The aperture is in fluid communication with the first lumen. The protrusion reinforces an area surrounding the aperture.

An ultrasonic tip is for use with a surgical handpiece to produce both longitudinal and torsional motion, the handpiece including an ultrasonic transducer. The ultrasonic tip comprises a shaft, a cutting feature and a protrusion. The shaft extends between a proximal end and a distal end. The proximal end has a first cross-sectional area. The distal end has a second cross-sectional area. The first cross-sectional area is greater than the second cross-sectional area. The cutting feature is coupled to the distal end of the shaft. An aspiration lumen is defined by the shaft. The aspiration lumen is configured to extend along a longitudinal axis of the shaft. The aspiration lumen is configured to be placed in fluid communication with the handpiece. The protrusion is on the shaft and is positioned between the distal end and the proximal end. A portion of the protrusion has a third cross-sectional area. The third cross-sectional area is less than the first cross-sectional area. The third cross-sectional area is greater than the second cross-sectional area. An aperture is defined by the protrusion and in fluid communication with the aspiration lumen. The protrusion reinforces an area surrounding the aperture.

An ultrasonic tip is for use with a surgical handpiece to produce both longitudinal and torsional motion, the handpiece including an ultrasonic transducer disposed within a housing. The ultrasonic tip comprises a shaft, a cutting feature and a protrusion. The shaft has a longitudinal axis extending between a proximal end and a distal end. The proximal end has a first diameter and the distal end has a second diameter. The first diameter is greater than the second diameter. The cutting feature is coupled to the distal end of the shaft. An aspiration lumen is defined by the shaft. The aspiration lumen is configured to extend along the longitudinal axis of the shaft. The aspiration lumen is configured to be placed in fluid communication with the handpiece. The protrusion is on the shaft and is positioned between the distal end and the proximal end. A portion of the protrusion has a third diameter. The third diameter is less than the first diameter. The third diameter is greater than the second diameter. An aperture is defined by the protrusion and is in fluid communication with the aspiration lumen. The protrusion reinforces an area surrounding the aperture.

Figure 2:
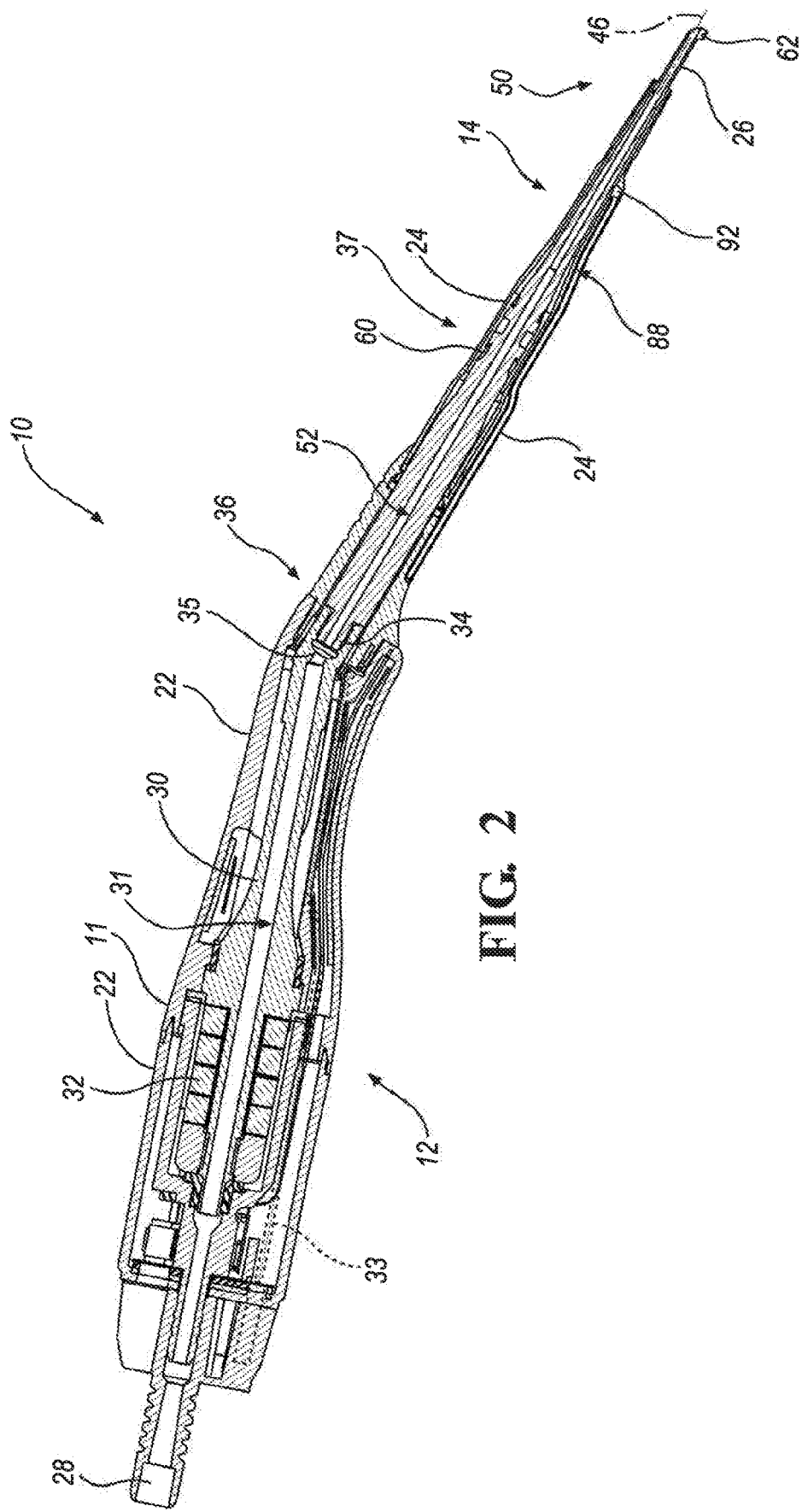
FIG. 2 is a sectional view of the ultrasonic surgical handpiece assembly of FIG. 1 in the direction of section line arrows 2.

FIGS. 1 and 2 illustrate an exemplary configuration of an ultrasonic surgical handpiece assembly 10, which may comprise part of an ultrasonic cutting system 12, that may be utilized by a medical professional to remove biological material from a patient. The ultrasonic surgical handpiece assembly 10 may comprise an ultrasonic handpiece 11 including a proximal housing portion 22 and a distal housing portion 20. An irrigation sleeve 24 may be removably coupled to the distal housing portion 20 of the ultrasonic surgical handpiece 11. The irrigation sleeve 24 and an ultrasonic tip 26, alternatively identified herein as a cutting tip 26, may be configured such that the irrigation sleeve 24 surrounds at least a portion of the ultrasonic tip 26 along a length of the ultrasonic tip 26 when both the irrigation sleeve 24 and the ultrasonic tip 26 are coupled to the ultrasonic handpiece 11. The irrigation sleeve 24 and the ultrasonic tip 26 may at least in part comprise an ultrasonic sleeve assembly 14.

FIG. 2 illustrates a sectional view of the ultrasonic surgical handpiece assembly 10 of FIG. 1. As illustrated in FIG. 2, the ultrasonic handpiece 11 may comprise a transducer 32, which may be an ultrasonic transducer 32, disposed within a void defined by the distal housing portion 20 and the proximal housing portion 22 of the ultrasonic handpiece 11. The transducer 32 may comprise a piezoelectric element or a magnetostrictive element configured to generate mechanical energy.

The ultrasonic handpiece 11 may also comprise a horn 30 that may be at least partially disposed within the void defined by the distal housing portion 20 and the proximal housing portion 22 of the ultrasonic handpiece 11. The horn 30 may comprise a distal end and a proximal end. The proximal end of the horn 30 may be coupled to a distal end of the transducer 32. The transducer 32 may be configured to provide the mechanical energy generated by the piezoelectric element or magnetostrictive element to the horn 30. The horn 30 may also be configured to define a horn lumen 31 that extends from the distal end to the proximal end of the horn 30 for fluid connection to a nipple 28 at a proximal end 16 of the proximal housing portion 22. The nipple 28 may be used to connect the handpiece 11 to a vacuum source (not shown). The horn lumen 31 may define a portion of a passageway that extends through the ultrasonic handpiece 11 to provide aspiration to the ultrasonic tip 26.

The ultrasonic handpiece 11 may further comprise an irrigation line 33 that is disposed within the void defined by the distal housing portion 20 and the proximal housing portion 22 of the ultrasonic handpiece 11. The irrigation line 33 may be configured to extend from the proximal end 16 to the distal end of the ultrasonic handpiece 11. The irrigation line 33 may serve to channel water from an irrigation system that is coupled to the ultrasonic handpiece 11 through the ultrasonic handpiece 11 to the irrigation sleeve 24. It should be appreciated that the irrigation line 33 may route directly from an irrigation source (not shown) to the ultrasonic sleeve (i.e., the irrigation line need not be always routed through the handpiece).

The ultrasonic tip 26 may comprise a shaft 48 that comprises a distal region 50, alternatively referenced to herein as a distal end 50, an intermediate region 37, and a proximal region 36, alternatively reference to herein as a proximal region 36. The shaft also has a distal end and a proximal end, with the proximal region being adjacent the proximal end and the distal region being adjacent the distal end. The ultrasonic tip may also comprise a coupling feature 34 positioned at the proximal region 36 of the shaft 48 and is configured to couple the proximal region 36 of the ultrasonic tip 26 to the distal end of the horn 30 to allow the horn 30 to be in mechanical communication with the ultrasonic tip 26. The coupling feature 34 may be a threaded coupler configured to engage a corresponding threaded coupler 35 on the distal end of the horn 30. The ultrasonic tip 26 may be threaded into the horn 30 and tightened to a predetermined torque specification to removably secure the ultrasonic tip 26 to the ultrasonic handpiece 11. While not illustrated in the figures, it is contemplated that the coupling feature 34 may be configured as a quick connection, quarter turn fitting, or similar coupling mechanism. It is further contemplated that the coupling feature 34 may be configured to permanently affix the ultrasonic tip 26 to the handpiece 11. For example, the ultrasonic tip 26 may be coupled to the ultrasonic handpiece 11 by a weld, epoxy, or similar coupling method. Alternatively, it is also contemplated that the ultrasonic tip 26 and the horn 30 may be formed as a unitary component.

The shaft 48 of the ultrasonic tip 26 may also be configured to define an aspiration lumen 52 that extends from the proximal region 36, through the intermediate region 37, to the distal region 50 of the ultrasonic tip 26. The aspiration lumen 52 may be oriented to be generally parallel to and may extend along a longitudinal axis. The aspiration lumen 52 of the ultrasonic tip 26 may be configured to form a fluid passageway with the lumen 31 of the horn 30 when the ultrasonic tip 26 is coupled to the horn 30. Otherwise stated, the aspiration lumen 52 may be configured to be placed in fluid communication with the handpiece 11, and the lumen 31 of the horn 30 in particular. The aspiration lumen 52 is open at the distal region 50 of the shaft 48. The aspiration lumen 52 of the ultrasonic tip 26 may be configured to provide aspiration away from the surgical site. For example, the aspiration lumen 52 may be used to vacuum fluid and biological tissue away from the distal end 50 of the ultrasonic tip 26. The aspiration lumen 52 may be in fluid communication with a lumen defined by the cutting feature 62.

Figure 3:
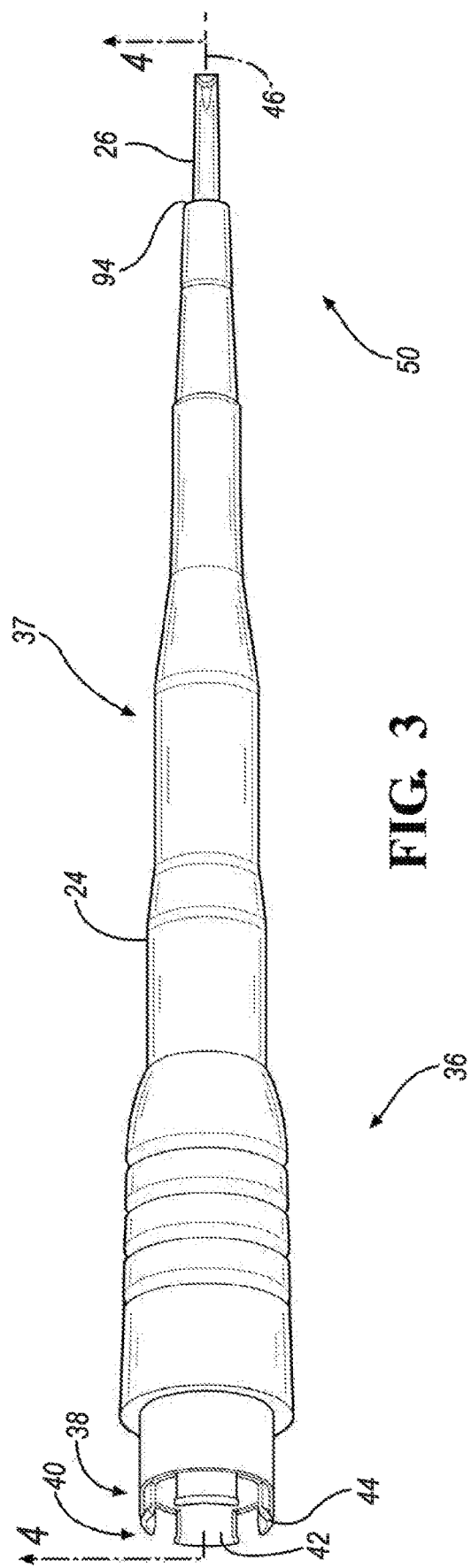
FIG. 3 is a top, angled view of an ultrasonic tip and an irrigation sleeve with the ultrasonic tip positioned within the irrigation sleeve.

FIG. 3 illustrates a top view of an exemplary configuration of the irrigation sleeve 24 having a distal end 94 and a proximal end. The irrigation sleeve 24 may comprise an irrigation sleeve coupling mechanism 38 on the proximal end of the irrigation sleeve 24. The irrigation sleeve coupling mechanism 38 may comprise one or more fingers 42 extending proximally from the proximal end of the irrigation sleeve 24. Each of the one or more fingers 42 may comprise a tab 44 extending in a radially outward direction relative to the longitudinal axis 46 of the irrigation sleeve 24. The fingers 42 act as the male fitting configured to couple with a female fitting (not shown) on the handpiece 11 to create a snap-fit 40 or interference fit. It is contemplated that other types of irrigation sleeve coupling mechanisms 38 may be used to couple the irrigation sleeve 24 to the ultrasonic handpiece 11. For example, the irrigation sleeve coupling mechanisms 38 may be configured as a threaded connection.

Figure 4:
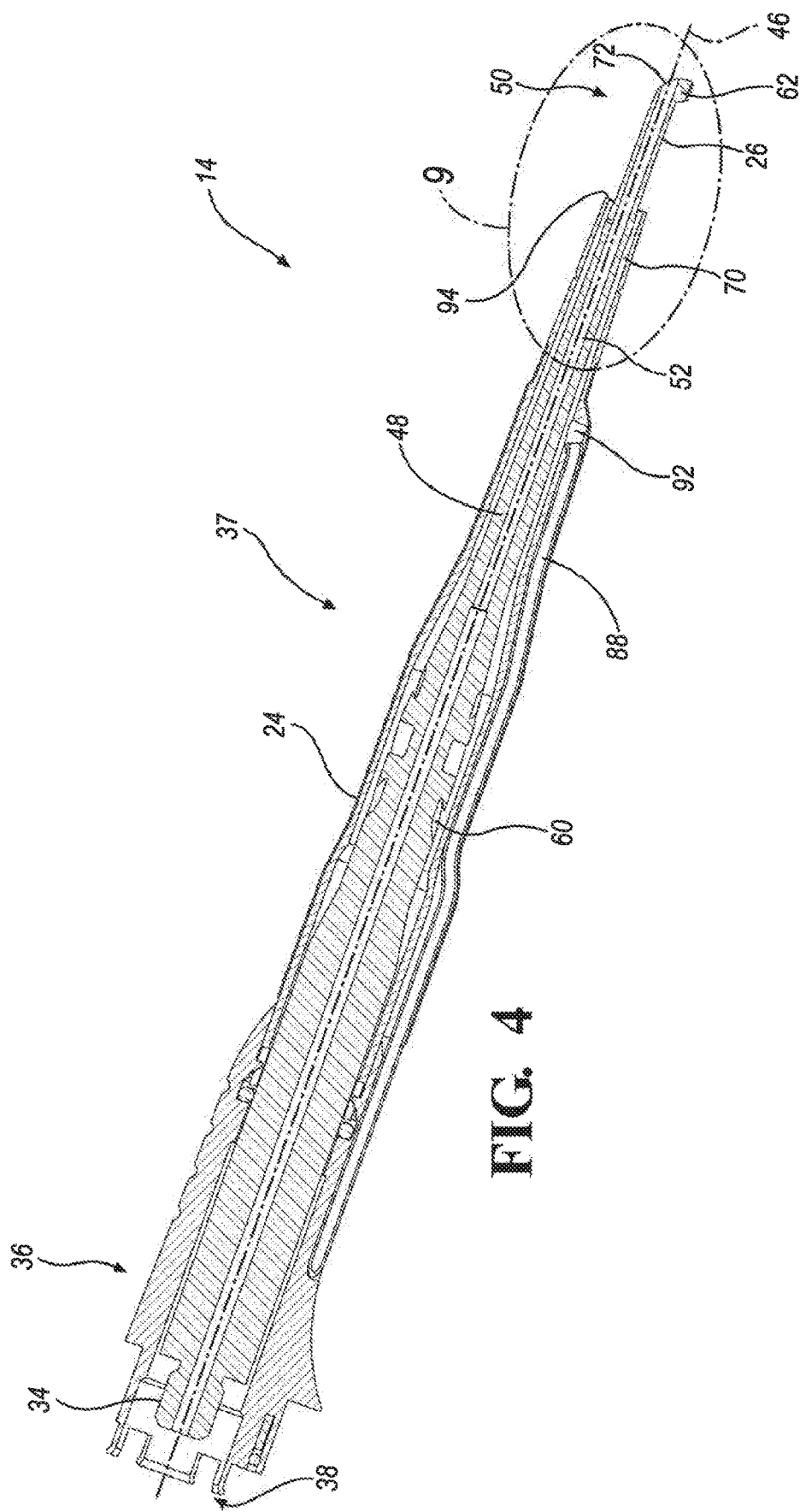
FIG. 4 is sectional view of the ultrasonic tip and the irrigation sleeve of FIG. 3 in the direction of section line arrows 4.

Referring to FIG. 4, a sectional view of the ultrasonic tip 26 at least partially disposed within a lumen 70 defined by the irrigation sleeve 24 is illustrated. The irrigation sleeve 24 may comprise an irrigation channel 88 that has a proximal end and a distal end. The proximal end of the irrigation channel 88 may be configured to couple to the distal end of the irrigation line 33 of the ultrasonic handpiece 11 or irrigation source. The irrigation channel 88 may be configured to run adjacent to the lumen 70 defined by the irrigation sleeve 24 and terminating at a port 92 disposed on the surface of the lumen 70 to provide irrigation fluid from the ultrasonic handpiece 11 to the ultrasonic tip 26 and the surgical site. The position of the port 92 may vary. For example, the port 92 may be adjacent the proximal end of the sleeve 24. Alternatively, the position of the port may be adjacent the distal end of the sleeve.

Figure 5:
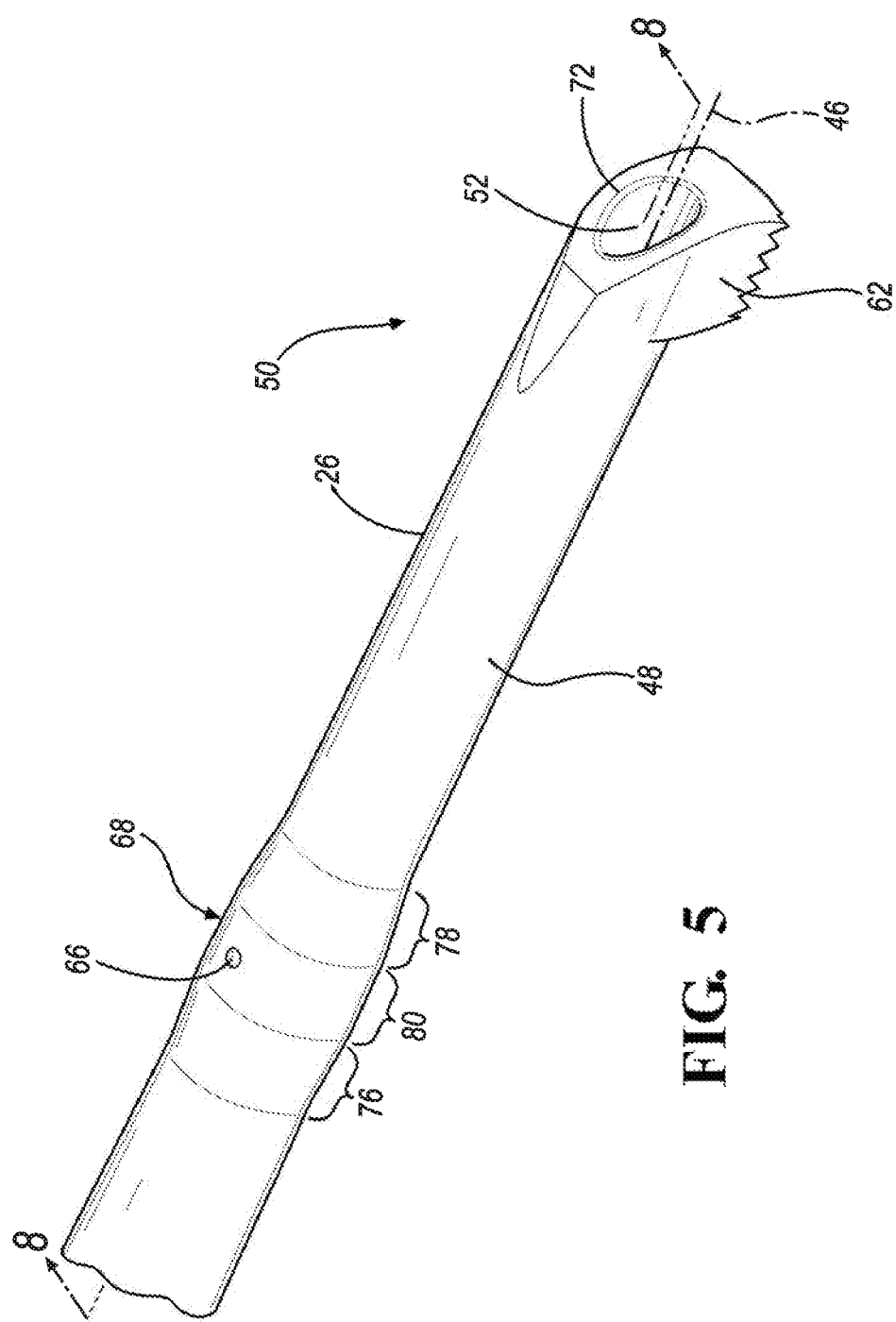
FIG. 5 is a perspective view of a distal portion of the ultrasonic tip including a protrusion and a cutting feature.

Referring to FIG. 5, a portion of the distal region of the ultrasonic tip 26 is illustrated. The shaft 48 of the ultrasonic tip 26 may comprise a protrusion 68 at an intermediate point on the shaft 48 between the proximal region 36 and the distal region 50 of the ultrasonic tip 26. The protrusion 68 may be configured to extend radially about the shaft 48 of the ultrasonic tip 26. The protrusion 68 may comprise a first taper region 76, a median region 80, and a second taper region 78. The median region 80 is positioned between the first taper region 76 and the second taper region 78. In an exemplary configuration, the first taper region 76 may have a positive slope on the proximal side of the protrusion 68, and the second taper region 78 may have a negative slope on the distal side of said protrusion 68 relative to the longitudinal axis of the lumen of the shaft. The median region 80 may have no slope and may be parallel with respect to the longitudinal axis 46. In another configuration, the protrusion 68 may comprise a generally rounded or hemispherical geometry at the transition from the first taper region 76 to the median region 80 and then the second taper region 78. The diameter and cross-sectional area of the first taper region 76 and the second taper region 78 is less than the diameter and cross-sectional area of the median region 80. In another configuration, the protrusion 68 may comprise other multi-faceted shapes, not shown. The protrusion 68 may be configured to have a progressive transition from the first taper region 76 to the median region 80 and then from the median region 80 to the second taper region 78. The progressive transition of the protrusion 68 may reduce the likelihood of creating an additional stress point in the shaft 48 that may have a higher probability of failure during ultrasonic vibration. Additionally, the progressive transition prevents disturbances of the fluid flow patterns about the ultrasonic tip 26 as the fluid moves distally 50 relative to the ultrasonic tip 26 from between the irrigation sleeve 24 and the ultrasonic tip 26 from the irrigation port 92. The progressive transition also allows for the ultrasonic tip 26 to be used at high power without experiencing high stress to the point that could cause breakage of the ultrasonic tip 26. The progressive transition may also improve the properties of the shaft 48 to allow the ultrasonic tip 26 to be operated at optimal frequencies.

The shaft 48 may be free from any abrupt steps from the length associated with diameter D4 to the length associated with diameter D5 and/or the length associated with diameter D3 to the length associated with D5. Free from any abrupt steps should mean that the angle of the slope of each of the transition regions is lower than 10, or 5 degrees relative to the external surface of the shaft 48.

The ultrasonic tip 26 may further comprise the aperture 66 in the shaft 48. The protrusion 68 defines the aperture 66, typically in the median region 80 of the protrusion 68. The aperture 66 is in fluid communication with the aspiration lumen 52. The axis of the aperture 66 may be transverse to the longitudinal axis 46 of the ultrasonic tip 26. In one configuration, the axis of the aperture 66 may be perpendicular to the longitudinal axis 46. The diameter of the aperture 66 is smaller than the diameter of the aspiration lumen 52.

The protrusion 68 reinforces the area of the shaft 48 near the aperture 66. Because the aperture 66 otherwise weakens the strength of the shaft 48 by the aperture 66, a thicker third diameter D3 of the shaft 48 at the protrusion 68 and may help to increase the structural integrity of the ultrasonic tip 26 when the ultrasonic tip 26 is subjected to ultrasonic movements in the torsional and longitudinal directions during use.

Figure 8:
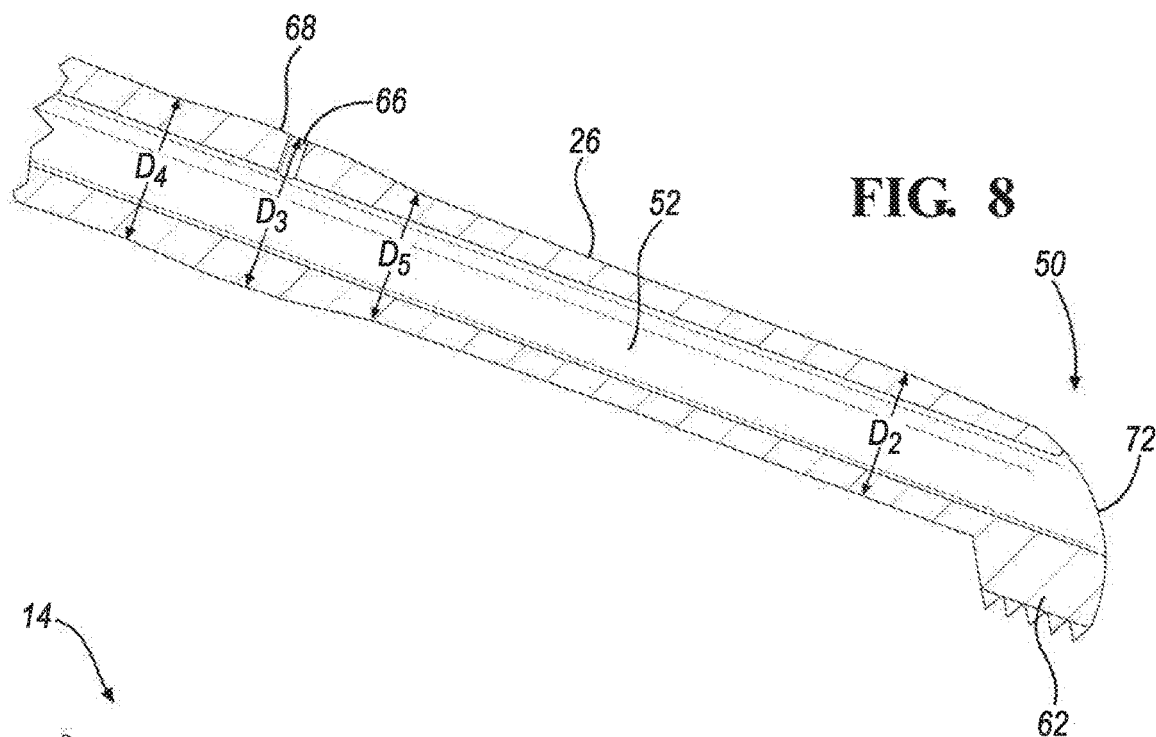
FIG. 8 is a sectional view of the distal portion of the ultrasonic tip of FIG. 5, including the protrusion and the cutting feature in the direction of section line arrows 8.
Figure 9:
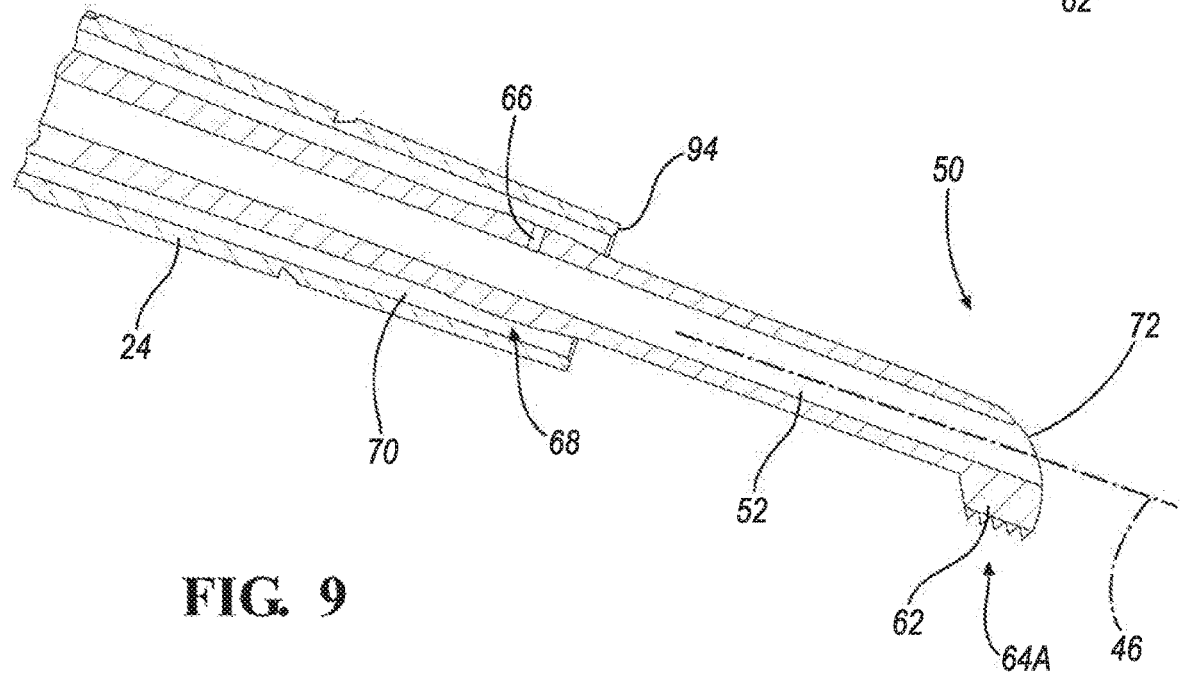
FIG. 9 is an enlarged sectional view of a distal portion of ultrasonic tip and the irrigation sleeve of a portion of FIG. 4 in oval 9.

The cutting feature 62 and an aspiration lumen opening 72 may be positioned at the distal end of the shaft 48. FIGS. 8 and 9 illustrate the aspiration lumen opening 72 being open on the distal region 50 of the shaft 48 and/or cutting feature 62. The aspiration lumen opening 72 may be used to remove excess fluid and/or biological debris from the surgical site.

In certain configurations, the dimension of the protrusion 68 are configured based on the dimensions of the aperture 66. For example, the axial length of the median region 80 may be between 200-1000% larger than the diameter of the aperture 66. In other configurations, the axial length of the median region 80 may be between 500-800% larger than the diameter of the aperture 66. Similarly, the length of the first and second tapered regions (76, 78) may also be related to the diameter of the aperture 66. For example, the combined axial length of the first tapered region 76, the median region 80, and the second tapered region 78 may be between 15000 and 24000% larger than the diameter of the aperture 66. These dimensions ensure that the tip achieves the precise balance of stress reduction and cutting performance.

For example, the length of the protrusion 68 (i.e., the distance between the line at 6E and 6F in FIG. 6A) may be approximately 2 mm, and could be between 1 mm and 6 mm in other configurations. The axial length (from the length at D4 to the length at D5) and radial thickness of the protrusion 68 may be related to the amount of material removed to create the aperture. For example, if the aperture 66 were to have a larger diameter, the diameter of the protrusion 68 and thickness would be greater. Conversely, if the aperture 66 were to have a smaller diameter, the thickness and length of the protrusion 68 would be less.

Figure 6A:
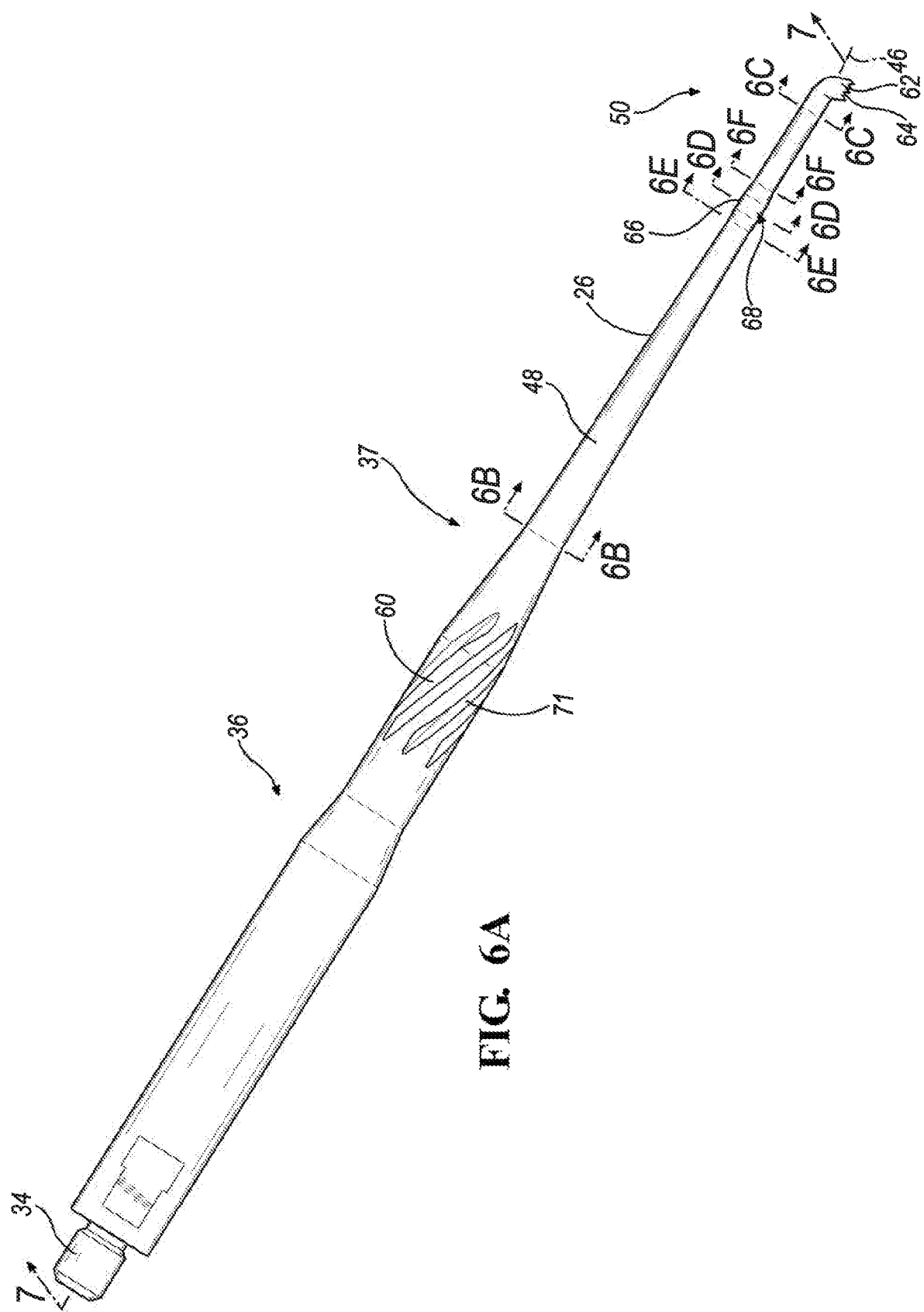
FIG. 6A is a side view of a first configuration of an ultrasonic tip including the protrusion and cutting feature.
Figure 7:
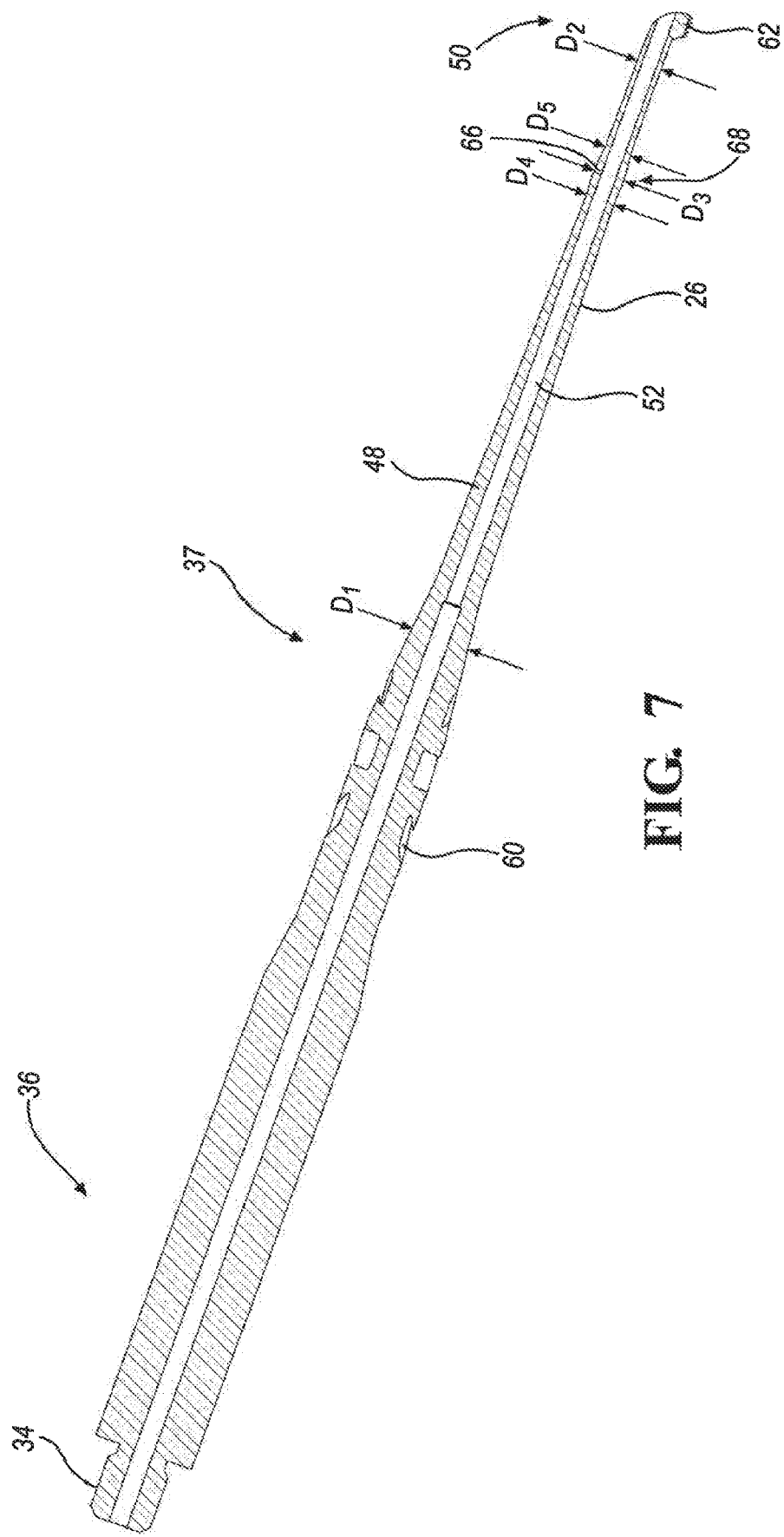
FIG. 7 is a sectional view of the ultrasonic tip of FIG. 6A in the direction of section line arrows 7.

FIGS. 7 and 8 show the ultrasonic tip 26 comprising the shaft 48 and a protrusion 68 on the shaft 48 positioned between the distal region 50 and the proximal region 36. The protrusion 68 is positioned distal to the vibration conversion mechanism 60 along the longitudinal axis 46, as shown in FIG. 6A. The shaft 48 at the protrusion 68 may have a third diameter D3 that is less than the first diameter D1 at the intermediate region 37 and greater than the second diameter D2 at the distal region 50.

As illustrated in FIGS. 6A-7, the diameter of the ultrasonic tip 26 varies from the proximal region 36, through the intermediate region 37, to the distal region 50 of the shaft 48. The shaft 48 comprises a first diameter D1 and comprises a second diameter D2, wherein the first diameter D1 is greater than the second diameter D2. The diameter D1 is positioned in the intermediate region 37 of the shaft 48 and the diameter D2 is positioned in the distal region 50 of the shaft.

The shaft 48 may be generally tapered along the longitudinal axis 46 from the proximal region 36, through the intermediate region 37, to the distal region 50. For example, the diameter of the shaft 48 may become smaller distally along the shaft 48 from the proximal region 36 to the distal region 50. One of a number of advantages provided by a tapered shaft 48, as it may reduce the size of the tip proximate and improve the user's line of sight while using the ultrasonic tip 26.

The shaft 48 may be made of a metal material such as titanium alloy, stainless steel, etc. or a non-metallic material such as a composite, depending on the application. In one example of the shaft 48, and ultrasonic tip 26 may be integral, unitary, and one-piece. In another example, the distal end 50 of the ultrasonic tip 26 may be attached to the shaft 48 by a suitable mechanism such as threads (not shown). It should be appreciated that metals are known in the art regarding high power ultrasonic components. It should also be appreciated that the diameters of the distal region 50 of the shaft 48 and the ultrasonic tip 26 have a relatively small diameter, for example less than one centimeter (1 cm), so as to work in a small opening of the patient. It should further be appreciated that the shaft 48 and the ultrasonic tip 26 may be scaled larger or smaller depending on the application.

Referring to FIG. 6A, the ultrasonic tip 26 further comprises a vibration conversion mechanism 60 for converting a vibration energy transmitted from the ultrasonic transducer 32 into a composite vibration composed of a longitudinal vibration along a longitudinal axis 46 and a torsional vibration. The intermediate region 37 is distal the vibration conversion mechanism 60. The vibration conversion mechanism 60 may comprise one or more helical groove portions 71 on the surface of the shaft 48. These one or more groove portions 71 may be wound around a circumferential surface of the shaft 48, as shown. The vibration conversion mechanism 60 functions to convert the longitudinal vibration transmitted from the transducer 32 through the horn 30 into a composite vibration composed of a longitudinal vibration in the longitudinal axial 46 direction of the ultrasonic tip 26 and a torsional vibration having the longitudinal axis 46 of the ultrasonic tip 26 act as a fulcrum. It should be appreciated that the vibration conversion mechanism may alternatively take other forms suitable for converting a longitudinal motion into a composite motion. These alternative forms may be asymmetries in the cross-section shape of the shaft 48. Details regarding the vibration conversion mechanism may be found in U.S. Pat. Nos. 6,497,715; 6,955,680; and 6,984,220; which are hereby incorporated in by reference in their entirety.

FIG. 6A also shows the ultrasonic tip 26 comprising the shaft 48 and a cutting feature 62 coupled to the distal region 50 of the shaft 48. The cutting feature 62 may be the part of the ultrasonic tip 26 that dissects or cuts a patient's biological tissue. A range of different cutting features 62 may be coupled to the distal end 50 of the shaft 48. In one example, the cutting feature 62 may have a cutting face 64 facing in a direction at an angle equal to or less than 90 degrees relative to the longitudinal axis 46. The terms cutting face and cutting surface may be used interchangeably herein. The cutting face 64 may be positioned in a manner that the center of the cutting face 64 is on an opposing side of the shaft 48 relative to the aperture 66. The cutting feature may be configured to cut with torsional motion.

Figure 6B:
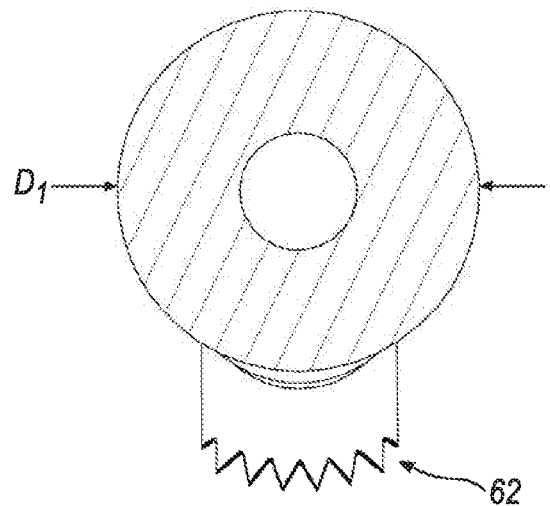
FIG. 6B is a cross-sectional view of the ultrasonic tip along the 6B axis of FIG. 6A in the direction of section line arrows 6B.
Figure 6C:
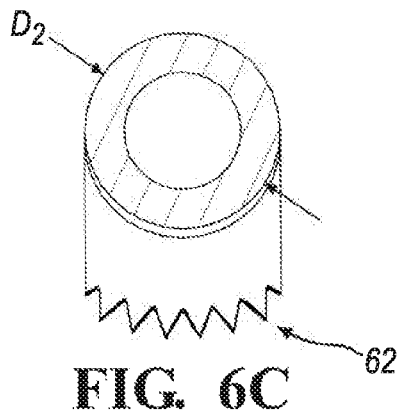
FIG. 6C is a cross-sectional view of the ultrasonic tip along the 6C axis of FIG. 6A in the direction of section line arrows 6C.
Figure 6D:
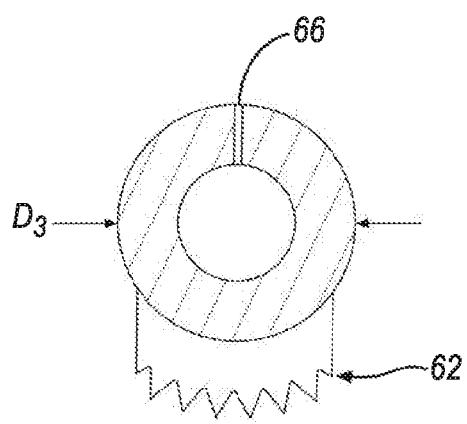
FIG. 6D is a cross-sectional view of the ultrasonic tip along the 6D axis shown in FIG. 6A in the direction of section line arrows 6D.
Figure 6E:
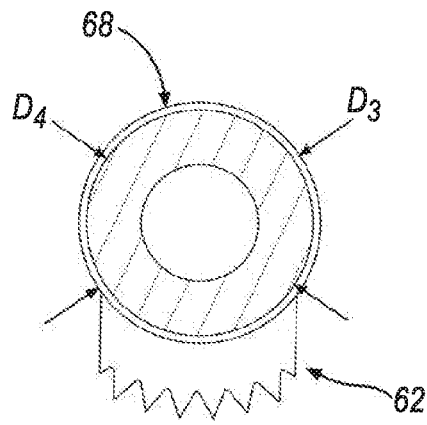
FIG. 6E is a cross-sectional view of the ultrasonic tip along the 6E axis shown in FIG. 6A in the direction of section line arrows 6E.
Figure 6F:
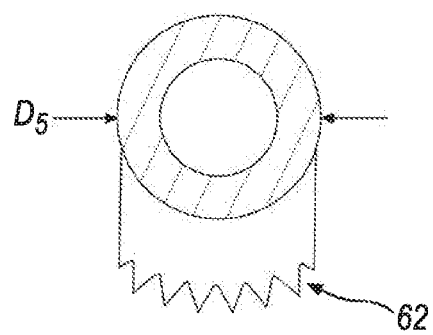
FIG. 6F is a cross-sectional view of the ultrasonic tip along the 6F axis shown in FIG. 6A in the direction of section line arrows 6F.

As shown in FIGS. 6B-6F, the shaft 48 may have a greater cross sectional area on the intermediate region 37 at location D1 than a cross sectional area at location D2. FIG. 6B shows the cross sectional area of the shaft 48 at location D1. FIG. 6C shows the cross sectional area of the shaft 48 at D2. Furthermore, FIG. 6D shows the cross sectional area of the shaft 48 at location D3 and also shows the aperture 66. As shown in FIG. 6E, the cross sectional area of D4 is less than the cross sectional area of D3. FIG. 6F shows the cross sectional area at location D5. When taking FIGS. 6B-6F together, this shows that the cross sectional area at location D3, which is near the protrusion 68, is greater than the cross sectional area at locations D4 and D5 which are proximally and distally adjacent to the protrusion, respectfully. The various cross-sectional area of the shaft 48 results in different strengths of the shaft 48 at various locations along the length. Generally, the greater cross-sectional area of the shaft 48 at a given location results in a greater wall thickness, which results in a greater strength.

As described above, the aperture 66 weakens the strength of the shaft 48. The greater cross sectional area at the protrusion 68 overcomes the weakness created by the aperture 66 to allow the ultrasonic tip 26 to be used at a higher power setting and not break from the increased stress. The cross sectional area of the protrusion 68 may be configured to have the least amount of area necessary to avoid inefficiencies and maintain line of sight, while maintaining necessary stress properties to prevent failure.

As shown in FIG. 8, the shaft 48 of the ultrasonic tip 26 has varying thicknesses.

Assuming the aspiration lumen 52 has a constant diameter from the distal region 50, through the intermediate region 37, to the proximal region 36, the thickness of shaft 48 at the aperture 66 is greater than the thickness of the shaft 48 at areas immediately adjacent to the aperture. Said another way, the shaft 48 thickness at the median region 80 is greater than the shaft 48 thickness at the first taper region 76 and the second taper region 78. The increased thickness of the shaft 48 at the median region 80 where the aperture 66 is located may improve the strength of the shaft 48.

As shown in FIG. 4, the irrigation sleeve 24 is configured to surround a portion of the shaft 48 in when the irrigation sleeve 24 and the ultrasonic tip 26 are coupled to the handpiece 11. The irrigation sleeve 24 comprises the lumen 70. The irrigation sleeve 24 has a proximal end 36 and the distal end 94. The proximal end 36 of the sleeve 24 includes the coupling mechanism 38 configured to removeably couple to the handpiece 11. The irrigation sleeve defines an irrigation channel 88 and is separate from the lumen 70. The irrigation channel 88 has a distal end and a proximal end, the proximal end of the irrigation channel 88 is configured to releasably couple to the irrigation source (not shown). The irrigation channel 88 may carry fluid to the lumen 70 through an irrigation port 92. The irrigation port 92 may be in fluid communication with the irrigation channel 88 and the lumen 70.

In certain configurations, the fluid may flow from the irrigation source (not shown) through the irrigation channel 88 to the irrigation port 92. The irrigation port 92 supplies fluid to the lumen 70 of the irrigation sleeve 24. Fluid in the lumen 70 of the irrigation sleeve 24 may flow distally towards the cutting tip 26. While the fluid is flowing toward the cutting tip 26 some fluid may enter the aspiration lumen 52 through the aperture 66 on the protrusion 68. The fluid flowing through the aperture 66 helps to reduce the temperature of the cutting tip 26 and may increase performance of the surgical handpiece assembly 10. Furthermore, it may alternatively help reduce the temperature of the sleeve 24, to thereby prevent tissue that comes into contact with the exterior surface of the sleeve from being inadvertently heated.

The irrigation sleeve 24 may be made from any polymer, for example a thermoplastic. The distal end 94 of the irrigation sleeve 24 may have a portion of frangible sections that could be cut or snipped to change the length of the irrigation sleeve 24.

The irrigation channel 88 may be in fluid communication with the handpiece 11 and/or an irrigation source (not shown). The combination of the aperture 66 on the shaft 48, the irrigation channel 88, the position of the distal end 94 of the sleeve 24 relative to the aperture 66, the irrigation port 92 and the aspiration lumen 52 improve the cooling ability of the ultrasonic tip 26. Additionally, the above referenced combination improves cooling of the ultrasonic tip 26 to prevent the irrigation sleeve 24 from becoming deformed or melting from excessive heat generated by the longitudinal and torsional motion of the ultrasonic tip 26.

As shown in FIG. 9, the irrigation sleeve 24 surrounds a portion of the ultrasonic tip 26 along the length of the ultrasonic tip. The distal end 94 of the irrigation sleeve 24 extends along the longitudinal axis 46 towards the distal region 50 of the ultrasonic tip 26. The distal end 94 of the irrigation sleeve 24 may extend beyond the aperture 66. The aperture 66 may have a proximal end and a distal end, the distal end 94 of the irrigation sleeve 24 extends beyond both the proximal side and the distal side of the aperture 66. In other words, the aperture 66 is completely covered by the sleeve 24 when the ultrasonic tip and the sleeve 24 are coupled to the handpiece 11. The fluid in the lumen 70 helps cool the ultrasonic tip 26 and the sleeve 24.

The ultrasonic tip 26 allows the efficient removal of bone with torsional or longitudinal motion of the instrument tip. The cutting feature 62 may comprise a cutting face 64A to aid in such removal. However, it should be appreciated that the ultrasonic tip 26 may also be used with transducers that vibrate longitudinally, torsionally, or a combination of both longitudinal and torsional motion. Furthermore, in some examples, the ultrasonic tip is free from the vibration conversion mechanism.

A torsional dissection tip is effective in the removal of bone, bony prominences, calcified neoplasm, cartilage, cartilaginous materials, intervertebral disc, and other pathologies when the cutting feature contacts such. The device is especially useful during neurosurgery, especially inside-out bone dissection once the superficial cortex has been removed, spinal surgery, orthopedic surgery, plastic/reconstructive surgery, and ear, nose, throat surgery, and other surgeries whereby the aforesaid tissues are encountered.

It is to be appreciated that the cutting features 62 of the ultrasonic tip 26 may have a plurality of configurations. Referring to FIGS. 10A-10E, various exemplary configurations of the cutting feature 62 of the ultrasonic tip 26 are illustrated. The cutting feature 62 may comprise a cutting face 64, wherein the cutting face 64 comprises one or more teeth 65. The teeth 65 of the cutting face 64 may be arranged wherein the teeth 65 are directed radially outward from the longitudinal axis 46 of the ultrasonic tip 26. For certain configurations the plane of the cutting feature is substantially parallel yet offset to the central axis of the distal end 50 of the instrument, however the position of the cutting face 64 can be varied in a virtually limitless manner.

Figure 10A:
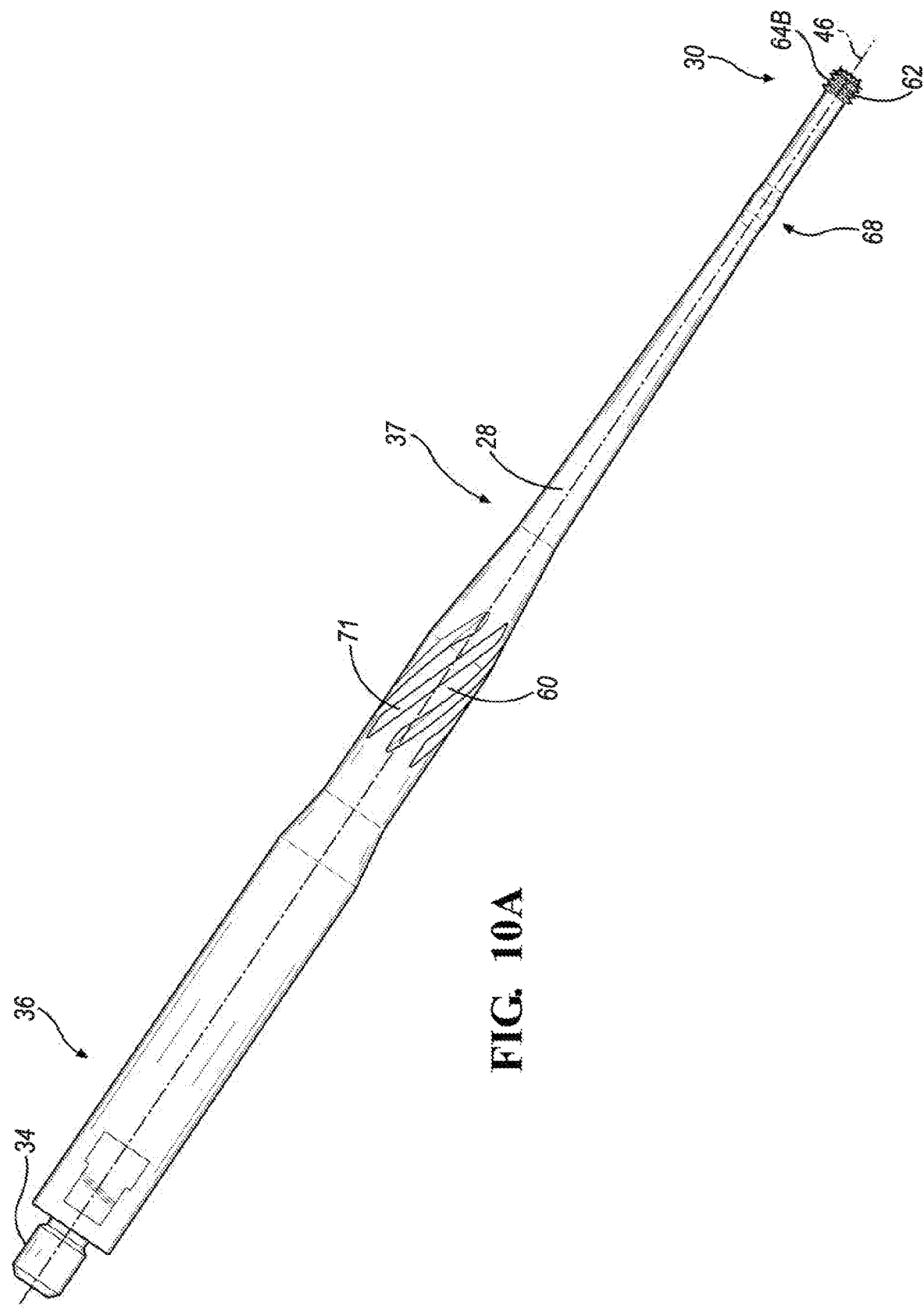
FIG. 10A is a bottom view of a first configuration of an ultrasonic tip including the protrusion and cutting feature.
Figure 10C:
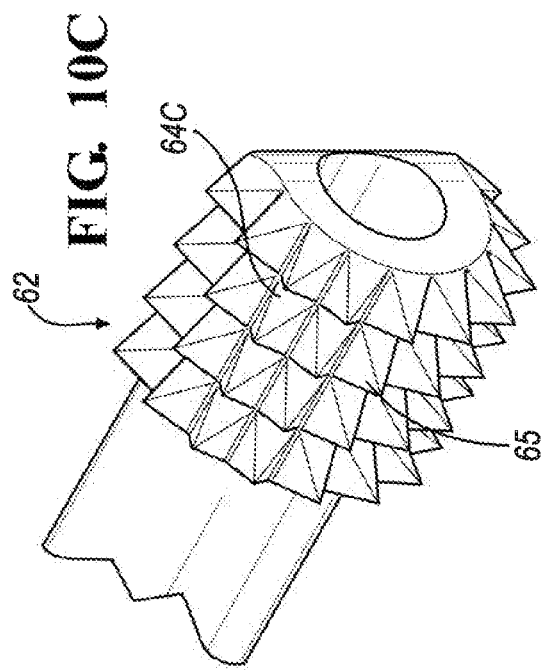
FIG. 10C is a perspective view of a second configuration of a cutting feature at the distal region of the ultrasonic tip of FIG. 10A.
Figure 10E:
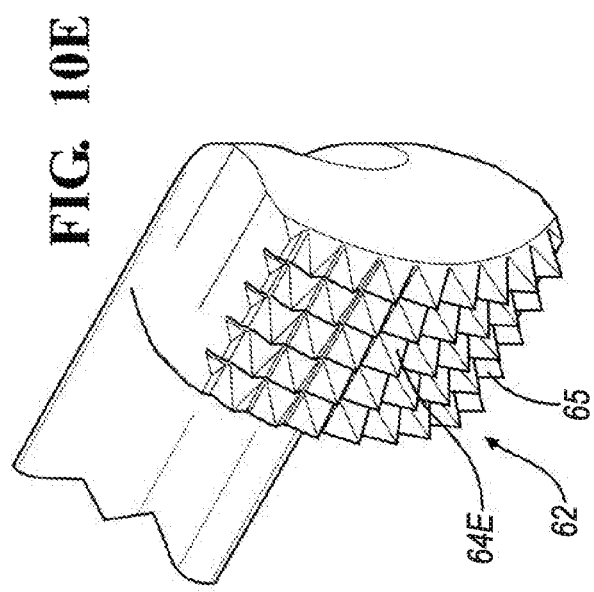
FIG. 10E is a perspective view of a fourth configuration of a cutting feature at the distal region of the ultrasonic tip of FIG. 10A.
Figure 10B:
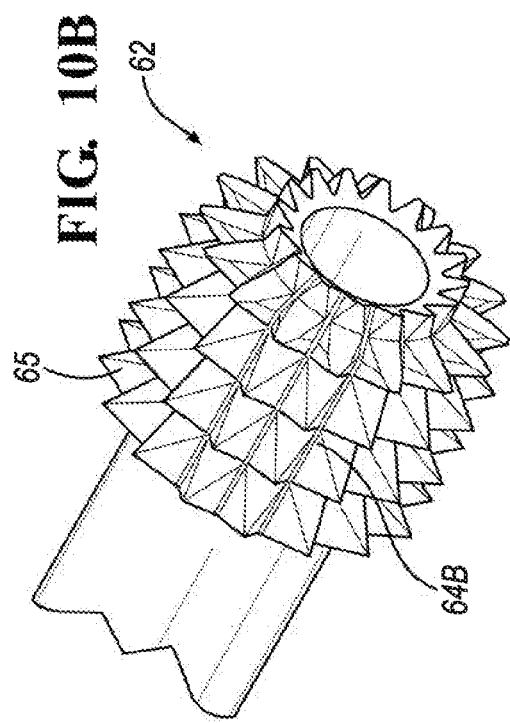
FIG. 10B is a perspective view of the first configuration of a cutting feature at the distal region of the ultrasonic tip of FIG. 10A.

Referring to FIG. 10B, a first configuration of the cutting feature 62 is illustrated. The first configuration of the cutting feature 62 comprises a cutting surface 64B that includes a plurality of teeth 65 disposed radially about the distal end 50 of the shaft 48. For example, the teeth 65 may configured to be directed outwardly from the longitudinal axis 46 of the ultrasonic tip 26, and the teeth 65 arrange to encircle the entire circumference of the distal end of the shaft 48. At least some of the teeth extend distally.

Alternatively, FIG. 10C illustrates a second configuration of the cutting feature 62. The second configuration of the cutting feature 62 comprises a cutting surface 64C comprising an arched or half cylinder-like shape that includes a plurality of teeth 65 directed outwardly from the longitudinal axis of the ultrasonic tip 26.

Figure 10D:
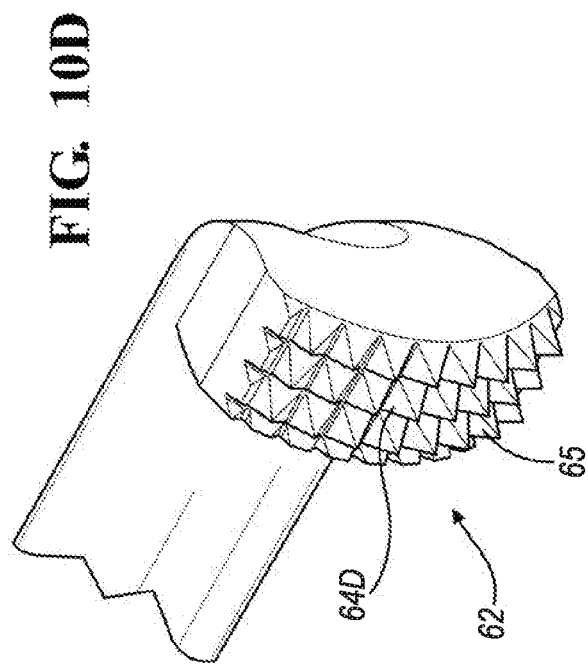
FIG. 10D is a perspective view of a third configuration of a cutting feature at the distal region of the ultrasonic tip of FIG. 10A.
Figure 11:
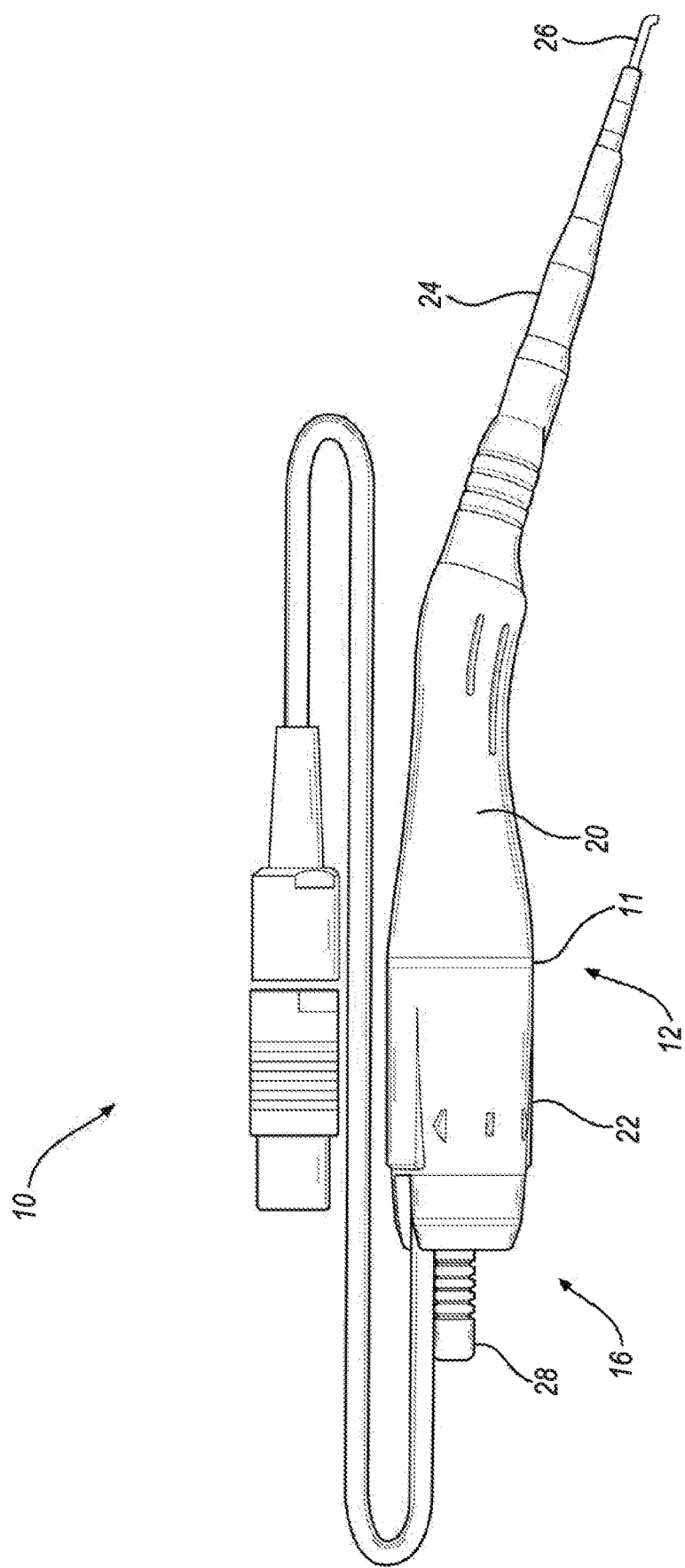
FIG. 11 is a side view of the ultrasonic surgical handpiece assembly of FIG. 1.

FIG. 10D illustrates a third configuration of the cutting feature 62. The third configuration of the cutting feature 62 comprises a cutting surface 64D comprising an arched or half cylinder-like shape that includes a plurality of teeth 65 directed outwardly from the longitudinal axis of the ultrasonic tip 26. The cutting surface 64D is generally offset from the shaft 48 of the ultrasonic tip 26 and oriented to be perpendicular to the longitudinal axis 46 of the ultrasonic tip 26.

FIG. 10E illustrates a fourth configuration of the cutting feature 62. The fourth configuration of the cutting feature 62 comprises a cutting surface 64E comprising an arched or half cylinder-like shape that includes a plurality of teeth 65 directed outwardly from the longitudinal axis of the ultrasonic tip 26. The cutting surface 64E is generally offset from the shaft of the ultrasonic tip 26 and oriented to be perpendicular to the longitudinal axis 46 of the ultrasonic tip 26. Other suitable cutting features are also contemplated, including those described in U.S. Pat. No. 8,512,340; and U.S. Publication 2018/0103976; which are hereby incorporated by reference in their entirety.

Several examples have been discussed in the foregoing description. However, the examples discussed herein are not intended to be exhaustive or limit the invention to any particular form. For example, while the example configurations describe the surgical instrument as an ultrasonic handpiece, it is further contemplated that the features and concepts described with regard to the ultrasonic handpiece may be applied to other medical or surgical instruments. This similarly applies to the ultrasonic tip, which may further include blades, drill bits, rotating burs, open-window shavers, and the like. The terminology which has been used is intended to be in the nature of words of description rather than of limitation. Many modifications and variations are possible in light of the above teachings and the invention may be practiced otherwise than as specifically described.

What is claimed is:

1. An ultrasonic tip for use with a surgical handpiece to produce both longitudinal and torsional motion, the handpiece including an ultrasonic transducer disposed within a housing, said ultrasonic tip comprising:
   a shaft having a longitudinal axis extending between a proximal end and a distal end, said proximal end having a first diameter and said distal end having a second diameter,
      wherein said first diameter is greater than said second diameter, and
      wherein said shaft comprises a vibration conversion mechanism for converting a vibration energy transmitted from the ultrasonic transducer into a composite vibration composed of a longitudinal vibration along the longitudinal axis and a torsional vibration;
   a cutting feature coupled to said distal end of said shaft;
   an aspiration lumen defined by said shaft, said aspiration lumen configured to extend along said longitudinal axis of said shaft, said aspiration lumen configured to be placed in fluid communication with the handpiece;
   a protrusion on said shaft and positioned between said distal end and said proximal end with said protrusion being positioned distal to said vibration conversion mechanism along said longitudinal axis, a portion of said protrusion having a third diameter, wherein said third diameter is less than said first diameter and said third diameter is greater than said second diameter; and
   an aperture defined by said protrusion in fluid communication with said aspiration lumen, wherein said protrusion reinforces an area surrounding the aperture,
   wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope.

2. The ultrasonic tip of claim 1, wherein said proximal end of said shaft comprises a coupling feature configured to removably couple said shaft to the transducer of the handpiece.

3. The ultrasonic tip of claim 2, wherein said coupling feature comprises a plurality of threads configured to couple to the transducer of the handpiece.

4. The ultrasonic tip of claim 1, wherein said vibration conversion mechanism comprises one or more helical groove portions formed on an external surface of said shaft.

5. The ultrasonic tip of claim 1, wherein said cutting feature comprises a cutting face facing in a direction at an angle equal or less than 90 degrees to said longitudinal axis.

6. The ultrasonic tip of claim 1, wherein said cutting feature has a cutting face arranged radially outward from said longitudinal axis wherein said cutting face comprising one or more teeth.

7. The ultrasonic tip of claim 1, wherein said aspiration lumen is open at said distal end and said proximal end of said shaft.

8. An ultrasonic sleeve assembly for use with a surgical handpiece comprising an ultrasonic transducer, said ultrasonic sleeve assembly comprising:
   a cutting tip comprising:
      a shaft having a longitudinal axis extending between a proximal end and a distal end, said proximal end comprising a coupling feature configured to removably couple said shaft to the handpiece, said proximal end comprising a first diameter and said distal end comprising a second diameter, wherein said first diameter is greater than said second diameter,
    wherein said shaft comprises a vibration conversion mechanism for converting a vibration energy transmitted from the ultrasonic transducer into a composite vibration composed of a longitudinal vibration along the longitudinal axis and a torsional vibration;
    a cutting feature coupled to said distal end of said shaft;
    an aspiration lumen defined by said shaft and configured to extend along said longitudinal axis of said shaft, said aspiration lumen configured to be in fluid communication with the surgical handpiece when said shaft is coupled to the surgical handpiece;
    a protrusion on said shaft positioned distal of said vibration conversion mechanism, wherein a portion of said protrusion having a third diameter, wherein said third diameter is less than said first diameter and said third diameter is greater than said second diameter, wherein said protrusion is configured to strengthen said shaft; and
    an aperture defined by said protrusion and in fluid communication with said aspiration lumen,
    wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope; and
    an irrigation sleeve configured to surround a portion of said shaft when said irrigation sleeve and said cutting tip are coupled to the handpiece, said irrigation sleeve defining a lumen comprising a proximal end and a distal end, said proximal end of said lumen comprising a coupling mechanism configured to removably couple to the handpiece,
    wherein said irrigation sleeve further defines an irrigation channel separate from said lumen, said irrigation channel having a distal end and a proximal end, said proximal end of said irrigation channel is configured to releasably couple to an irrigation source, said irrigation channel configured to carry fluid to said lumen through an irrigation port, said irrigation port in fluid communication with said irrigation channel and said lumen.

9. The ultrasonic sleeve assembly of claim 8, wherein said coupling feature comprises a plurality of threads configured to couple to the transducer of the handpiece.

10. The ultrasonic sleeve assembly of claim 8, wherein said vibration conversion mechanism comprises one or more helical groove portions formed on an external surface of said shaft.

11. The ultrasonic sleeve assembly of claim 8, wherein said cutting feature comprises a cutting face facing in a direction perpendicular to said longitudinal axis.

12. The ultrasonic sleeve assembly of claim 11, wherein said aperture is positioned in a radially opposed direction from said cutting face.

13. The ultrasonic sleeve assembly of claim 8, wherein said cutting feature has a cutting face arranged radially outward from said longitudinal axis, and wherein said cutting face comprises one or more teeth.

14. The ultrasonic sleeve assembly of claim 8, wherein said aspiration lumen is open at said distal end and said proximal end of said shaft.

15. An ultrasonic cutting system to produce both longitudinal and torsional motion, said ultrasonic cutting system comprising:
    a handpiece comprising a transducer disposed within a housing;
    a cutting tip coupled to said handpiece, said cutting tip comprising:
        a shaft having a longitudinal axis extending between a proximal end and a distal end, said proximal end comprising a coupling feature configured to removably couple said shaft to said handpiece, said proximal end comprising a first diameter and said distal end comprising a second diameter, wherein said first diameter is greater than said second diameter;
        a cutting feature coupled to said distal end of said shaft;
        an aspiration lumen defined by said shaft, said aspiration lumen configured to extend along the longitudinal axis of said shaft, said aspiration lumen in fluid communication with said handpiece;
        a protrusion on said shaft and positioned between said distal end and said proximal end, a portion of said protrusion having a third diameter, wherein said third diameter is less than said first diameter and said third diameter is greater than said second diameter; and
        an aperture defined by said protrusion and in fluid communication with said aspiration lumen, wherein said protrusion reinforces an area surrounding the aperture,
        wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope;
    an irrigation sleeve coupled to said handpiece, said irrigation sleeve surrounding a portion of said shaft and having a proximal end and a distal end, wherein said irrigation sleeve defines a lumen, said proximal end of said irrigation sleeve having a coupling mechanism configured to removably couple said irrigation sleeve to said handpiece,
        said irrigation sleeve further defining an irrigation channel comprising a distal end and a proximal end, said proximal end of said irrigation channel is configured to receive irrigation fluid from an irrigation source; and
    an irrigation port in fluid communication with said distal end of said irrigation channel, said irrigation port configured to dispense irrigation fluid toward said shaft,
    wherein said distal end of said irrigation sleeve is positioned proximal to said distal end of said shaft,
    wherein said irrigation port is positioned proximal relative to said aperture along said longitudinal axis, and
    wherein said distal end of the irrigation sleeve is distal to a distal end of said aperture such that said irrigation sleeve encompasses an entirety of said aperture.

16. The ultrasonic cutting system of claim 15, wherein said distal end of said irrigation sleeve extends beyond said distal end of said aperture in a distal direction along said longitudinal axis.

17. The ultrasonic cutting system of claim 15, wherein said coupling feature comprises a plurality of threads configured to couple to said transducer of said handpiece.

18. The ultrasonic cutting system of claim 15, wherein said shaft comprises a vibration conversion mechanism for converting a vibration energy transmitted from said transducer into a composite vibration composed of a longitudinal vibration along said longitudinal axis and a torsional vibration.

19. The ultrasonic cutting system of claim 18, wherein said vibration conversion mechanism comprising one or more helical groove portions formed on an external surface of said shaft.

20. The ultrasonic cutting system of claim 15, wherein said cutting feature comprises a cutting face facing in a direction perpendicular to said longitudinal axis.

21. The ultrasonic cutting system of claim 20, wherein said aperture is positioned in a radially opposed direction from said cutting face.

22. The ultrasonic cutting system of claim 15, wherein said cutting feature has a cutting face arranged radially outward from said longitudinal axis and wherein said cutting face comprises one or more teeth.

23. The ultrasonic cutting system of claim 15, wherein said aspiration lumen is open at said distal end and said proximal end of said shaft.

24. An ultrasonic tip for use with a surgical handpiece to produce both longitudinal and torsional motion, the handpiece including an ultrasonic transducer, said ultrasonic tip comprising:
a shaft extending between a proximal end and a distal end, said proximal end having a first cross-sectional area and said distal end having a second cross-sectional area, wherein said first cross-sectional area is greater than said second cross-sectional area,
wherein said shaft comprises a vibration conversion mechanism for converting a vibration energy transmitted from the ultrasonic transducer into a composite vibration composed of a longitudinal vibration along a longitudinal axis of said shaft and a torsional vibration; a cutting feature coupled to said distal end of said shaft;
an aspiration lumen defined by said shaft, said aspiration lumen configured to extend along said longitudinal axis of said shaft, said aspiration lumen configured to be placed in fluid communication with the handpiece;
a protrusion on said shaft and positioned between said distal end and said proximal end with said protrusion being positioned distal to said vibration conversion mechanism along said longitudinal axis, a portion of said protrusion having a third cross-sectional area, wherein said third cross-sectional area is less than said first cross-sectional area and said third cross-sectional area is greater than said second cross-sectional area; and
an aperture defined by said protrusion and in fluid communication with said aspiration lumen, wherein said protrusion reinforces an area surrounding the aperture,
wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope.

25. An ultrasonic tip for use with a surgical handpiece including an ultrasonic transducer disposed within a housing, said ultrasonic tip comprising:
a shaft comprising a distal region, an intermediate region, and a proximal region, said intermediate region having a first diameter and said distal region having a second diameter, wherein said first diameter is greater than said second diameter,
wherein said shaft comprises a vibration conversion mechanism for converting a vibration energy transmitted from the ultrasonic transducer into a composite vibration composed of a longitudinal vibration along a longitudinal axis of said shaft and a torsional vibration;
a cutting feature coupled to said distal region of said shaft;
a first lumen defined by said shaft, said first lumen configured to extend along said longitudinal axis of said shaft, said first lumen configured to be placed in fluid communication with the handpiece;
a protrusion on said shaft and positioned between said intermediate region and said distal region, said intermediate region being positioned between said protrusion and said vibration conversion mechanism, wherein a portion of said protrusion having a third diameter, wherein said third diameter is less than said first diameter and said third diameter is greater than said second diameter; and
an aperture defined by said protrusion in fluid communication with said first lumen, wherein said protrusion reinforces an area surrounding the aperture
wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope.

26. An ultrasonic tip for use with a surgical handpiece to produce both longitudinal and torsional motion, the handpiece including an ultrasonic transducer, said ultrasonic tip comprising:
a shaft extending between a proximal end and a distal end, said proximal end having a first cross-sectional area and said distal end having a second cross-sectional area, wherein said first cross-sectional area is greater than said second cross-sectional area,
a cutting feature coupled to said distal end of said shaft;
an aspiration lumen defined by said shaft, said aspiration lumen configured to extend along a longitudinal axis of said shaft, said aspiration lumen configured to be placed in fluid communication with the handpiece;
a protrusion on said shaft and positioned between said distal end and said proximal end, a portion of said protrusion having a third cross-sectional area, wherein said third cross-sectional area is less than said first cross-sectional area and said third cross-sectional area is greater than said second cross-sectional area; and
an aperture defined by said protrusion and in fluid communication with said aspiration lumen, wherein said protrusion reinforces an area surrounding the aperture,
wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope.

27. An ultrasonic tip for use with a surgical handpiece to produce both longitudinal and torsional motion, the handpiece including an ultrasonic transducer disposed within a housing, said ultrasonic tip comprising:
- a shaft having a longitudinal axis extending between a proximal end and a distal end, said proximal end having a first diameter and said distal end having a second diameter, wherein said first diameter is greater than said second diameter,
- a cutting feature coupled to said distal end of said shaft;
- an aspiration lumen defined by said shaft, said aspiration lumen configured to extend along said longitudinal axis of said shaft, said aspiration lumen configured to be placed in fluid communication with the handpiece;
- a protrusion on said shaft and positioned between said distal end and said proximal end, a portion of said protrusion having a third diameter, wherein said third diameter is less than said first diameter and said third diameter is greater than said second diameter; and
- an aperture defined by said protrusion in fluid communication with said aspiration lumen, wherein said protrusion reinforces an area surrounding the aperture,
- wherein said protrusion comprises a first taper region, a median region, and a second taper region, with an external surface of said median region being generally parallel to the longitudinal axis and said median region disposed between said first taper region and said second taper region, said first taper region being proximal to said median region and having a positive slope, and said second taper region being distal to said median region and having a negative slope.

* * * * *